(12) United States Patent
Miyai et al.

(10) Patent No.: US 8,329,641 B2
(45) Date of Patent: *Dec. 11, 2012

(54) REMEDIES FOR ISCHEMIC DISEASE OF THE LIMBS COMPRISING ADMINISTRATION OF G-CSF

(75) Inventors: Tatsuya Miyai, Tokyo (JP); Masahiko Tamura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 815 days.

This patent is subject to a terminal disclaimer.

(21) Appl. No.: 10/380,200

(22) PCT Filed: Sep. 13, 2001

(86) PCT No.: PCT/JP01/07946
§ 371 (c)(1),
(2), (4) Date: Mar. 13, 2003

(87) PCT Pub. No.: WO02/22163
PCT Pub. Date: Mar. 21, 2002

(65) Prior Publication Data
US 2005/0048026 A1    Mar. 3, 2005

(30) Foreign Application Priority Data
Sep. 13, 2000   (JP) ................ 2000-277562

(51) Int. Cl.
*A61P 9/10* (2006.01)
*A61K 38/18* (2006.01)
*C07K 14/535* (2006.01)

(52) U.S. Cl. .......... 514/1.9; 514/7.6; 514/9.7; 514/15.6; 514/21.2; 530/399

(58) Field of Classification Search .................. None
See application file for complete search history.

(56) References Cited

U.S. PATENT DOCUMENTS

| 7,473,425 B2 * | 1/2009 | Fukuda et al. ............. 424/184.1 |
| 2004/0009940 A1 | 1/2004 | Coleman et al. |
| 2004/0131585 A1 * | 7/2004 | Itescu ............... 424/85.1 |
| 2005/0048026 A1 | 3/2005 | Miyai et al. |

FOREIGN PATENT DOCUMENTS

| DE | 100 33 219 A1 | 1/2002 |
| EP | 0 357 240 | 3/1990 |

(Continued)

OTHER PUBLICATIONS

Frank, et al. Antimicr. Agents & Chemo. 40: 1308-1310, 1996 'Treatment of *Staphylococcus aureus* Catheter-related Infection and Infective Endocarditis with Granulocyte Colony-Stimulating Factor in the Experimental Rabbit Model'.*

(Continued)

*Primary Examiner* — Zachary Howard
(74) *Attorney, Agent, or Firm* — Browdy and Neimark, P.L.L.C.

(57) ABSTRACT

An effective agent for treating ischemic disease, the agent containing human granulocyte colony-stimulating factor (human G-CSF) as an active ingredient is disclosed. By administering this therapeutic agent, an effective therapy particularly for obstructive arteriosclerosis is provided which can eliminate drawbacks with conventional therapies, such as kinesitherapy, pharmacotherapy, and revascularization, and recently proposed therapies, such as gene therapy and intramuscular transplantation of bone marrow cells. Furthermore, the therapeutic agent can be used as an agent for treating ischemic disease, such as ischemic cerebrovascular disorder or ischemic heart disease.

6 Claims, 1 Drawing Sheet

FOREIGN PATENT DOCUMENTS

| | | |
|---|---|---|
| WO | WO 99/17798 | 4/1999 |
| WO | WO 99/17798 A1 | 4/1999 |
| WO | WO 99/45775 | 9/1999 |
| WO | WO 99/45775 A1 | 9/1999 |
| WO | WO 01/94420 A1 | 12/2001 |

OTHER PUBLICATIONS

Ishida, 2005. Circ J. 69: 1260-1265.*
Huang, 2005. Diabetes Care. 28(9): 2155-2160.*
Gupta et al, 2005. 81: 236-242.*
Markkanen et al, 2005. Cardiovascular Research. 65: 656-664.*
Squadrito et al, 1997. 120(2): 333-9.*
Sullivan et al. 1993. Vet Surg. 22(5): 343-350.*
Shi et al. 1998. Blood. 92(2): 362-367.*
Asahara et al. 1999. Circulation Reserach. 85: 221-228.*
Peichev et al. 2000. Blood. 95(3): 952-958.*
Takahashi et al (1999. Nature Medicine. 5(4): 434-438).*
Ieda et al. 2007. Journal of Molecular and Cellular Cardiology. 42: 540-548.*
Gough et al, 1997. The Lancet. 350: 855-859.*
Hooi et al, 1999. British Journal of General Practice. 49: 49-55.*
Hilleman et al. 1998. Am J Health-Syst Pharm. 55(1): S21-S27.*
Campbell, 1993. Ann Pharmacother. 27: 1099-1105.*
Orlic et al, "Mobilized bone marrow cells repair the infarcted heart, improving function and survival", Proc. Natl. Acad. Sci. Col. 98, No. 18, pp. 10344-10349. Aug. 2001.
Theocharis et al, "Effect of Granulocyte Colony-Stimulating-Factor Administration on Tissue Regeneration Due to Thioacetamide-Induced Liver Injury in Rats", Digestive Diseases and Sciences, vol. 44, No. 10, pp. 1990-1996. Oct. 1999.
Theocharis et al, "Effect of two forms of granulocyte-colony-stimulating factor on hepatic regeneration after 70% partial hepatectomy in rats", Clinical Science, vol. 92, pp. 315-320. 1997.
Orlic, et al, "Bone marrow cells regenerate infarcted myocardium", Nature, vol. 410, pp. 701-705. Apr. 2001.
Penn et al, "Autologous cell transplantation for the treatment of damaged myocardium", Progress in Cardiovascular Diseases, vol. 45, No. 1, pp. 21-32. Jul./Aug. 2002.
Jackson, et al, "Regeneration of ischemic cardiac muscle and vascular endothelium by adult stem cells", Journal of Clinical Investigation. vol. 107, No. 11. Jun. 2001.
Stamm, et al, "Autologous bone-marrow stem-cell transplantation for myocardial regeneration", The Lancet, vol. 361, pp. 45-46. Jan. 2003.
Rafii, et al, "Contribution of marrow-derived progenitors to vascular and cardiac regeneration", Cell & Development Biology, vol. 13, pp. 61-67. 2002.
Makino, et al, "Cardiomyocytes can be generated from marrow stromal cells in vitro", Journal of Clinical Investigation, vol. 103, No. 5, pp. 697-705. Mar. 1999.
Kamihata, et al, "Implantation of bone marrow mononuclear cells into Ischemic myocardium enhances collateral perfusion and regional function via side supply of angioblasts, angiogenic ligands, and cytokines", Circulation, vol. 104, pp. 1046-1052. 2001.
Tomita, Shinji, et al, "Autologous Transplantation of Bone Marrow Cels Improves Damaged Heart Function" Circulation, V. 100, Suppl. 19, pp. II-247 to II-256, 1999.
Kobayashi, Masanobu, et al, "Mobilization mechanisms of hematopoietic stem cells into peripheral blood", Igaku No Ayumi, v. 176, No. 9, pp. 558-560, 1996.
Squadrito F. et al, "The effects of recombinant human granulocyte-colony stimulating factor on vascular dysfunction and splanchnic ischaemia-reperfusion Injury", British Journal of Pharmacology, (1997), vol. 120, pp. 333-339.
Feldman et al; "Anti-TNFα Therapy Is Useful in Rheumatoid Arthritis and Crohn's Disease: Analysis of the Mechanism of Action Predicts Utility in Other Diseases"; *Transplantation Proceedings*, 30, pp. 4126-4127 (1998).
Hayashi et al.; Potential Role of Hepatocyte Growth Factor, a Novel Angiogenic Growth Factor, in Peripheral Arterial Disease, Downregulation of HGF in response to Hypoxia in Vascular Cells; 1999, pp. II-301-II-308.
Mestas et al; Of Mice and Not Men: Differences between mouse and Human Immunolgy; *The Journal of Immunology*, 2004, 172, pp. 2731-238.
Teuveson et al; "New Immunosuppressants: Testing and Development in Animal Models and the Clinic: with Special Reference to DSG"; *Immunological Review*, 1993, N136, pp. 101-107.
Van Noort et al; "Cell Biology of Autoimmune Diseases", *International Review of Sytology*, 1998, v. 178, pp. 127-204.
Parissis et al, "Hematopoietic Colony Stimulating Factors in Cardiovascular and Pulmonary Remodeling: Promoters or Inhibitors?", Current Pharmaceutical Design, 2006, vol. 12, No. 21, pp. 2689-2699.

* cited by examiner

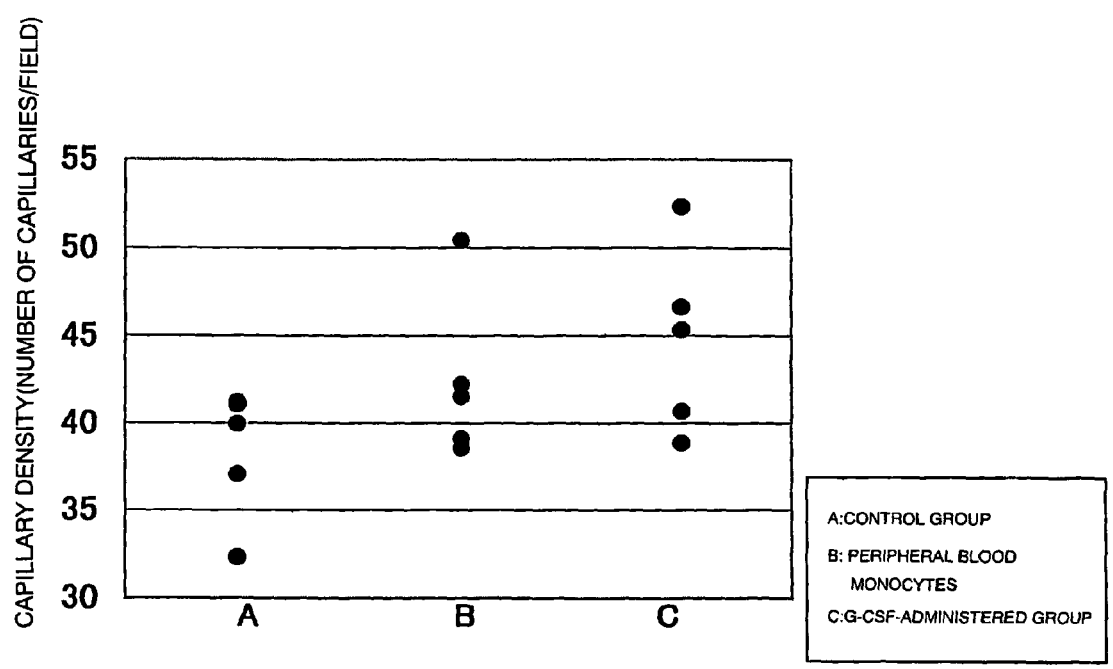

SEQUENCE LISTING

<160> NUMBER OF SEQ ID NOS: 1

<210> SEQ ID NO 1
<211> LENGTH: 174
<212> TYPE: PRT
<213> ORGANISM: Human

<400> SEQUENCE: 1

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

REMEDIES FOR ISCHEMIC DISEASE OF THE LIMBS COMPRISING ADMINISTRATION OF G-CSF

TECHNICAL FIELD

This invention relates to an agent for treating ischemic disease, the agent containing human granulocyte colony-stimulating factor (hereinafter referred to as human G-CSF) as an active ingredient.

BACKGROUND ART

The present invention concerns an agent for treating ischemic disease. A typical ischemic disease, obstructive arteriosclerosis, will be described first.

Obstructive arteriosclerosis is a disease in which an arteriosclerotic lesion results in occlusion or stenosis of a major truncal artery in the extremity, especially in the lower limb, causing an ischemic disorder to its periphery. Clinical symptoms of this disease are classified as coldness or numbness, intermittent claudication, rest pain, and ulcer/necrosis. In Japan, patients with obstructive arteriosclerosis are estimated to number about 100,000 (Yusuke Tada: Biomedicine & Therapeutics, Vol. 31, 289-292; 1997). The number of patients with this disease is expected to increase because of the increase in the elderly population and the westernization of diets. Therapies of obstructive arteriosclerosis include kinesitherapy or exercise therapy, pharmacotherapy, and revascularization, which are selected depending on symptoms or the patient's condition. Recently, gene therapy and intramuscular transplantation of bone marrow cells have also been attempted.

The above-described therapies are currently achieving some success in the treatment of obstructive arteriosclerosis, but the respective therapies involve the following problems. While exercise therapy has increased the distance (a patient can walk) of walking in some mild cases, the effect of this therapy is difficult to predict. Moreover, patients are not satisfied with the increase in the walking distance, if any, and 30% of them are reported to have requested revascularization (Takashi Ohta: Japan Medical Journal, Vol. 3935, 25-29, 1999). At present, exercise therapy is not a very effective form of treatment.

In pharmacotherapy, antiplatelet agents are mainly prescribed, but they merely prevent an aggravation of symptoms. Microcirculation improving agents and oxygen transport improving agents, which have recently been developed aggressively, are only expected to be indicated for mild cases. At present, there are no radical therapeutic agents available for obstructive arteriosclerosis.

Revascularization, on the other hand, is currently the most effective therapy, which involves percutaneous angioplasty or a bypass operation depending on the condition of the patient or the location or severity of the lesion. These surgical operations are so extensive as to pose problems, such as surgery-associated complications or deaths, and a poor prognosis for a long life.

With gene therapy, treatment is provided using genes of angiogenic factors, such as vascular endothelial cell growth factor and epidermal cell growth factor. However, this therapy is still at the experimental stage, and evaluations of its safety and efficacy have not been established. Thus, gene therapy has not spread generally.

Intramuscular transplantation of bone marrow cells, whose therapeutic effects have recently been reported, is a therapy in which bone marrow cells are transplanted into the muscle near the diseased part, whereafter they differentiate into vascular endothelial cells to form blood vessels. Although its efficacy will have to be evaluated in an increased number of patients, this therapy is expected to become a promising one, because it can treat severe cases. However, one of the problems with this therapy is considered to be a great burden associated with bone marrow harvest which falls on both the patients and the medical staffs.

Recent studies have shown that hematopoietic stem cells, which can differentiate into vascular endothelial cells, are present not only in the bone marrow, but also in the peripheral blood, and they take part in angiogenesis (Qun Shi et al. Blood Vol. 92, 362-367;1998, Takayuki Asahara et al. Circulation Research Vol. 85, 221-228;1999, Mario Peichev et al. Blood Vol. 95, 952-958;2000). (The hematopoietic stem cells are called "precursor cells for endothelial cells" from the viewpoint of the function of differentiating into endothelial cells. However, these cells are originally derived from hematopoietic stem cells. Thus, the term "hematopoietic stem cells" is used herein in accordance with the concept that they are a cell population capable of becoming endothelial cells.) Hence, hematopoietic stem cells in the peripheral blood are harvested and transplanted into the muscle close to the diseased part, whereby treatment of obstructive arteriosclerosis can be expected. This procedure is advantageous in that the burden imposed on the patient and medical staff at the time of taking peripheral blood stem cells is less than that during transplantation of stem cells in the bone marrow. Normally, however, the frequency of hematopoietic stem cells in the peripheral blood is extremely low. Thus, it is highly questionable whether a necessary and adequate amount of hematopoietic stem cells for the treatment of obstructive arteriosclerosis can be obtained.

DISCLOSURE OF THE INVENTION

Human G-CSF is a hematopoietic factor discovered as a differentiation/proliferation factor for progenitor cells of the granulocytic lineage. It is clinically applied as an agent for treating neutropenia following bone marrow transplantation or cancer chemotherapy, because it facilitates neutrophilic hematopoiesis in vivo. In addition to this action, transplantation of the peripheral blood stem cells mobilized by human G-CSF, i.e. peripheral blood stem cell transplantation, is conducted in the clinical setting for the purpose of accelerating hematopoietic recovery in the cancer patients after intensive chemotherapy. This hematopoietic stem cell mobilizing action of G-CSF is far more potent than that of GM-CSF, also a hematopoietic factor for the granulocytic lineage. In terms of few side effects as well, G-CSF has superiority over GM-CSF.

Prior to treatment with intramuscular transplantation of bone marrow cells in patients with obstructive arteriosclerosis, administration of human G-CSF can be expected to increase the frequency of hematopoietic stem cells in the bone marrow. Thus, the number of bone marrow punctures for harvesting bone marrow cells can be reduced, and the burden on the patient can be reduced. On this occasion, the burden on the patient and the medical staff can be further reduced by obtaining hematopoietic stem cells for transplantation from the peripheral blood. Furthermore, hematopoietic stem cells in the peripheral blood have been shown to contribute to blood vessel formation, and therefore it is expected that an increase of hematopoietic stem cells in the peripheral blood induced by the administration of human G-CSF will promote blood vessel formation. Hence, the mere administration of human G-CSF to patients can be expected to treat obstructive arteriosclerosis. Such treatment of obstructive arteriosclerosis by the administration of human G-CSF will clearly reduce the burden on the patient and the medical staff markedly in that it obviates the need for harvest and transplantation of hematopoietic stem cells.

BRIEF DESCRIPTION OF THE DRAWING

FIG. 1 is a view showing the effects of (B) inoculation of peripheral blood mononuclear cells derived from G-CSF-treated mice and (C) administration of G-CSF, on the density of capillaries in the rat ischemic limb. The capillary densities of the individual animals were plotted for B Group, C Group and Control Group (A).

The three modes of treatment for obstructive arteriosclerosis using human G-CSF described above can be expected to take effect in severe cases, and will be of great benefit to patients. If this treatment is combined with treatment with an angiogenic factor which promotes differentiation and growth of vascular endothelial precursor cells, such as vascular endothelial growth factor (VEGF), epidermal growth factor (EGF), hepatocyte growth factor (HGF), or fibroblast growth factor (FGF), or with the gene therapy of these factors, the therapeutic effect of that treatment is expected to be augmented further. In this case, these factors or their genes can be administered to patients, for example, to sites near the diseased part. Similarly, G-CSF is expected to show an increased therapeutic effect, when combined with agents clinically used as drug therapies for obstructive arteriosclerosis, such as anti-platelet agents, vasodilators, microcirculation improvers, anticoagulants, and antilipemic agents.

Besides, G-CSF of the present invention is applicable as an agent for treatment of other diseases classified as ischemic diseases. These diseases include the following: trauma, rejection reaction during transplantation, ischemic cerebrovascular disorder (e.g., apoplexy, cerebral infarction), ischemic renal disease, ischemic pulmonary disease, infection-related ischemic disease, ischemic disease of limbs, ischemic heart disease (ischemic cardiomyopathy, myocardial infarction, ischemic heart failure). That is, the present invention provides agents containing G-CSF as active ingredients for treatment of these diseases.

As a result of the foregoing investigations, we have accomplished the present invention. Namely, the present invention provides agents for treatment of ischemic disease which contain human G-CSF as active ingredients.

The present invention will be described in detail below.

EMBODIMENTS OF THE INVENTION

Human G-CSF is a protein having an amino acid sequence shown in Formula 1 below. Human G-CSF used in the present invention includes, in addition to this protein, a mutant protein which is produced by introducing some alterations of the amino acids, such a substitution, addition or deletion to the original protein. Alternatively, the human G-CSF according to the present invention may be the protein of Formula 1 or its mutant version described above with or without various modifications. As long as the products have G-CSF activity, they can be applied to the present invention. Herein, "various modifications" refer to structural transformation, addition and deletion of a sugar chain, and binding of inorganic or organic compounds, such as polyethylene glycol and vitamin B12.

Formula 1: Amino acid sequence SEQ ID NO: 1 of human G-CSF

| | | | | | | | | | | | | | | | |
|---|---|---|---|---|---|---|---|---|---|---|---|---|---|---|---|
| Thr | Pro | Leu | Gly | Pro | Ala | Ser | Ser | Leu | Pro | Gln | Ser | Phe | Leu | Leu | Lys | 16 |
| Cys | Leu | Glu | Gln | Val | Arg | Lys | Ile | Gln | Gly | Asp | Gly | Ala | Ala | Leu | Gln | 32 |
| Glu | Lys | Leu | Cys | Ala | Thr | Tyr | Lys | Leu | Cys | His | Pro | Glu | Glu | Leu | Val | 48 |
| Leu | Leu | Gly | His | Ser | Leu | Gly | Ile | Pro | Trp | Ala | Pro | Leu | Ser | Ser | Cys | 64 |
| Pro | Ser | Gln | Ala | Leu | Gln | Leu | Ala | Gly | Cys | Leu | Ser | Gln | Leu | His | Ser | 80 |
| Gly | Leu | Phe | Leu | Tyr | Gln | Gly | Leu | Leu | Gln | Ala | Leu | Glu | Gly | Ile | Ser | 96 |
| Pro | Glu | Leu | Gly | Pro | Thr | Leu | Asp | Thr | Leu | Gln | Leu | Asp | Val | Ala | Asp | 112 |
| Phe | Ala | Thr | Thr | Ile | Trp | Gln | Gln | Met | Glu | Glu | Leu | Gly | Met | Ala | Pro | 128 |
| Ala | Leu | Gln | Pro | Thr | Gln | Gly | Ala | Met | Pro | Ala | Phe | Ala | Ser | Ala | Phe | 144 |
| Gln | Arg | Arg | Ala | Gly | Gly | Val | Leu | Val | Ala | Ser | His | Leu | Gln | Ser | Phe | 160 |
| Leu | Glu | Val | Ser | Tyr | Arg | Val | Leu | Arg | His | Leu | Ala | Gln | Pro | | | 174 |

A method for producing this human G-CSF may be any method which can give the product defined above. Concretely, the human G-CSF is produced using human G-CSF-producing tumor, human G-CSF-producing hybridoma, or a transformed host which has been granted a G-CSF-producing potential by genetic recombination. Depending on the structure of human G-CSF to be produced, a changing operation or various modifying operations are appropriately applied at a suitable stage of the production process. If the human G-CSF is to be produced by genetic recombination, any routinely used host can be employed, such as *Escherichia coli* or animal cells.

The agent for treating ischemic disease according to the present invention can contain pharmaceutical carriers and vehicles necessary for assuming the form of a medicinal pharmaceutical composition, and can further contain stabilizers and adsorption preventing agents. Suitable dosage forms can be selected, including injections, sustained release preparations, transnasal preparations, oral preparations, transpulmonary preparations, transdermal preparations, and transmucosal preparations. If desired, suitable devices can be used.

The dose and the frequency of dosing of human G-CSF contained in the agent for treating ischemic diseases according to the present invention can be determined in consideration of the condition of the patient for whom the agent is indicated. The dose is usually 0.1 to 500 µg/kg/day, preferably 1 to 50 µg/kg/day, per adult. As the frequency of dosing, the agent of the invention can be administered for 1 to 7 days weekly. The mode of administration preferably includes intravenous administration, subcutaneous administration, and intramuscular administration. However, the present invention is not limited by the dose of human G-CSF, and can be combined with drugs hitherto used with effectiveness against obstructive arteriosclerosis, such as antiplatelet agents, vasodilators, microcirculation improvers, anticoagulants, and antilipemic agents, and can also be used in combination with gene therapy.

The present invention will be described in more detail with reference to Experimental Examples (pharmacological efficacy) and Examples for working of the invention (Preparation Examples), which in no way limited to the present invention.

EXPERIMENTAL EXAMPLE 1

Pharmacological Efficacy

The left femoral artery and vein of nude mice (BALB/cAJcl-nu) were ligated and then removed to prepare lower limb ischemia models. In an untreated group, the lower limb dropped out in 3 of 5 animals (60%) and became necrotic in 2 animals (40%) two weeks after ischemic treatment. In a group subcutaneously administered 100 µg/kg/day of G-CSF a total of 5 times from 3 days before creation of lower limb ischemia until 1 postoperative day, the fall and the necrosis of the lower limb were observed in 1 (20%) and 3 (60%) animals out of 5, respectives, and no damage was observed in 1 animal (20%), at 2 weeks post ischemic treatment. Thus the lower limb damage was reduced in the G-CSF treated group. These findings show that G-CSF may have the action of alleviating lower limb damage after ischemia by promoting angiogenesis.

EXPERIMENTAL EXAMPLE 2

Pharmacological Efficacy

After 100 µg/kg/day of G-CSF was subcutaneously administered to mice (BALB/cA) for 5 days, blood was taken, and a mononuclear cell fraction was obtained by the density gradient method (d=1.077). Also, the left femoral artery and vein of nude rats (F344/N Jcl-rnu) were removed to prepare lower limb ischemia models. One day after creation of ischemia, peripheral blood mononuclear cells from the G-CSF-treated mice were intramuscularly inoculated in a dose of $2 \times 10^7$ cells/head (corresponding to about 5 ml of peripheral blood) to the ischemic limb of the lower limb ischemia nude rat. A control group received in intramuscular administration of phosphate buffer. One week after inoculation, a tissue specimen of the lower limb was prepared, and the density of capillaries was measured after an alkaline phosphatase stain. As a result, the capillary density tended to be higher in the peripheral mononuclear cell treatment group than in the control group (control group: 38.3±1.7, peripheral mononuclear cell treatment group: 42.3±2.1, number of capillaries/field, 5 animals per group, mean±standard error). The results are shown in A and B of FIG. 1.

These findings show the possibility that G-CSF promoted the mobilization of endothelial precursor cells to the mouse peripheral blood, thereby promoting angiogenesis in the rats receiving a transplant of the peripheral mononuclear cell, and suggest the possibility of application of G-CSF to the treatment of peripheral circulatory disturbance.

EXPERIMENTAL EXAMPLE 3

Pharmacological Efficacy

The left femoral artery and vein of nude rats (F344/N Jcl-rnu) were removed to prepare lower limb ischemia models. The density of capillaries was measured by alkaline phosphatase stain of a lower limb tissue specimen prepared one week after creation of ischemia. Comparisons were made between a group subcutaneously administered 100 µg/kg/day of G-CSF from 4 days before creation of ischemia until one week after creation of ischemia (G-CSF treatment group) and a control group. The control group received an intramuscular administration of phosphate buffer. As a result, the capillary density was shown to be higher in the G-CSF treatment group than in the control group (control group: 38.3±1.7, G-CSF treatment group: 44.7±2.4, number of capillaries/field, 5 animals per group, mean±standard error). The results are shown in A and C of FIG. 1.

These results suggest that G-CSF has the effect of promoting angiogenesis at the site of ischemia, and suggest the possibility of application of G-CSF to the treatment of peripheral circulatory disturbance.

EXAMPLE 1

Preparation Example

Polysorbate 20 (Tween 20: polyoxyethylene sorbitan monolaurate), a nonionic surfactant, was added in an amount of 0.1 mg/ml to 50 µg/ml of human G-CSF (10 mM phosphate buffer, pH 7.0), and the mixture was adjusted to an osmotic pressure of 1 using NaCl. Then, the mixed solution was sterilized by filtration through a membrane filter having a pore size of 0.22 mm. The resulting solution was charged into a sterilized vial, whereafter the filled vial was capped with a similarly sterilized rubber stopper and then seamed with an aluminum cap to obtain a pharmaceutical solution for injection. This preparation for injection was stored in a cold dark place at 10° C. or lower.

EXAMPLE 2

Preparation Example

Polysorbate 80 (Tween 80: polyoxyethylene sorbitan monooleate), a nonionic surfactant, was added in an amount of 0.1 mg/ml to 100 µg/ml of human G-CSF (10 mM phosphate buffer, pH 7.0), and the mixture was adjusted to an osmotic pressure of 1 using NaCl. Then, the mixed solution was sterilized by filtration through a membrane filter having a pore size of 0.22 mm. The resulting solution was charged into a sterilized vial, whereafter the filled vial was capped with a similarly sterilized rubber stopper and then seamed with an aluminum cap to obtain a pharmaceutical solution for injection. This preparation for injection was stored in a cold dark place at 10° C. or lower.

EXAMPLE 3

Preparation Example

Polysorbate 20 (Tween 20: polyoxyethylene sorbitan monolaurate), a nonionic surfactant, in an amount of 0.1 mg/ml, 10 mg/ml of HAS and 50 mg/ml of mannitol were added to 50 µg/ml of human G-CSF (10 mM phosphate buffer, pH 7.0), followed by dissolving the mixture. Then, the solution was sterilized by filtration through a membrane filter having a pore size of 0.22 mm. The resulting solution was charged into a sterilized vial, whereafter the filled vial was half capped with a similarly sterilized rubber stopper and lyophilized to obtain a lyophilized preparation for injection. This lyophilized preparation for injection was stored under temperature conditions at room temperature or lower, and should be dissolved, before use, with distilled water for injection.

INDUSTRIAL APPLICABILITY

The agent for treating ischemic disease according to the present invention, which contains human G-CSF as an active ingredient, is expected to show a therapeutic effect in relatively severe cases of obstructive arteriosclerosis, as demonstrated in Experimental Examples 1 to 3. This effect of G-CSF is inferred to be based on the promotion of angiogenesis. Thus, G-CSF is expected to be therapeutically effective against other ischemic diseases, namely, trauma, rejection reaction during transplantation, ischemic cerebrovascular disorder (apoplexy, cerebral infarction), ischemic renal disease, ischemic pulmonary disease, infection-related ischemic disease, ischemic disease of limbs, and ischemic heart disease (ischemic cardiomyopathy, myocardial infarction, ischemic heart failure). The therapies according to the present invention are convenient, safe and efficacious as compared with conventional therapies.

---

The invention claimed is:

1. A method for treating obstructive arteriosclerosis of a limb, which comprises:

administering, directly to a patient in need of treatment of obstructive arteriosclerosis of a limb, a sufficient amount of human granulocyte colony-stimulating factor for such treatment, without harvesting and transplanting of hematopoietic stem cells, and determining alleviation of obstructive arteriosclerosis of the limb by measuring the quantity of obstructive arteriosclerosis of the limb following administration of granulocyte colony-stimulating factor, wherein a decrease in the quantity of obstructive arteriosclerosis of the limb following administration of granulocyte colony-stimulating factor as compared to prior to said administration indicates alleviation of obstructive arteriosclerosis of the limb.

2. The method according to claim 1, characterized in that hematopoietic stem cells increased in peripheral blood upon administration of the human granulocyte colony-stimulating factor contribute to angiogenesis of a diseased part of the limb.

3. The method according to claim 1, which further comprises administering a drug selected from the group consisting of an antiplatelet agent, vasodilator, an anticoagulant, and an antilipemic agent.

4. The method according to claim 3, wherein said administering of said human granulocyte colony-stimulating factor is carried out at a site near the diseased part of the limb by injection or transdermal application.

5. The method of claim 4, wherein said administering of said human granulocyte colony-stimulating factor is by injection, and said injection is by intravenous injection, subcutaneous injection or intramuscular injection.

6. The method of claim 1, wherein the quantity of obstructive arteriosclerosis of the limb is measured by measuring the density of capillaries of the limb, wherein an increase in density of capillaries of the limb following administration of granulocyte colony-stimulating factor as compared to prior to said administration indicates the decrease in the quantity of obstructive arteriosclerosis of the limb following administration of granulocyte colony-stimulating factor as compared to prior to said administration.

* * * * *